United States Patent [19]

Rempfler et al.

[11] Patent Number: 4,802,909
[45] Date of Patent: Feb. 7, 1989

[54] UREAS AND THEIR USE AS HERBICIDES

[75] Inventors: Hermann Rempfler, Ettingen; Erich Stamm, Huttwil; Rudolph C. Thummel, Courgenay, all of Switzerland

[73] Assignee: Ciba-Geigy Corporation, Ardsley, N.Y.

[21] Appl. No.: 107,437

[22] Filed: Oct. 9, 1987

[30] Foreign Application Priority Data

Oct. 13, 1986 [CH] Switzerland .......................... 4074/86
Jul. 28, 1987 [CH] Switzerland .......................... 2869/87

[51] Int. Cl.$^4$ .................... A01N 43/54; C07D 239/42
[52] U.S. Cl. ........................................ 71/92; 544/321; 544/323; 544/332
[58] Field of Search .................... 544/321, 332, 323; 71/92

[56] References Cited

U.S. PATENT DOCUMENTS 4,694,009  9/1987  Hubele et al. .................... 544/332

FOREIGN PATENT DOCUMENTS 135472  3/1985  European Pat. Off. ............ 544/321
151404  10/1981  German Democratic Rep. .................................... 544/321

OTHER PUBLICATIONS

Streitwieser, Organic Chemistry, 1976, p. 495.

Primary Examiner—Mary C. Lee
Assistant Examiner—J. Richter
Attorney, Agent, or Firm—Kevin T. Mansfield; Edward McC. Roberts

[57] ABSTRACT

The invention relates to ureas having a herbicidal and plant growth-regulating action of the formula

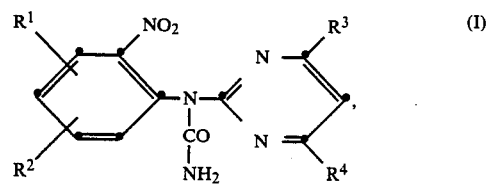

in which
$R^1$ and $R^2$ each represents, independently of the other, hydrogen, halogen, $C_1$–$C_6$-alkyl $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkoxy-($C_1$–$C_4$)-alkyl, nitro or cyano, and
$R^3$ and $R^4$ each represents, independently of the other, hydrogen, halogen, cyano, OH, SH, $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, mono-$C_1$–$C_4$-alkylamino, di-$C_1$–$C_4$-alkylamino, $C_1$–$C_4$-alkoxycarbonyl or $C_1$–$C_4$-alkoxy-($C_1$–$C_4$)-alkyl, processes and intermediates for the preparation thereof, and herbicidal and plant growth-regulating compositions containing a compound of the formula I.

14 Claims, No Drawings

UREAS AND THEIR USE AS HERBICIDES

The present invention relates to novel N-(2-nitrophenyl)-N-pyrimidin-2-ylureas having a herbicidal and plant growth-regulating action, agrochemical compositions that contain these substances as active ingredients, the use of the novel ureas for controlling weeds or for regulating plant growth, and processes for the preparation of the novel compounds. In addition, the invention also relates to novel intermediates and processes for the preparation thereof.

(Pyrimidin-2-yl)-2-nitroanilines are known from Patent Specification DD-151 404 and European patent application EP-A-O 172 786. These compounds are fungicidally active. In contrast, it has surprisingly been found that N-pyrimidin-2-yl-N-2-nitrophenylureas have a herbicidal and plant growth-regulating action.

The invention thus relates to ureas of the formula

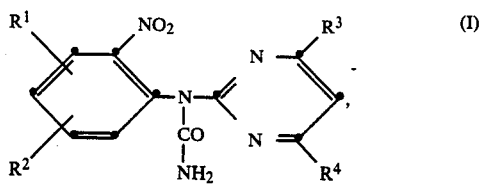

in which
$R^1$ and $R^2$ each represents, independently of the other, hydrogen, halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkoxy-($C_1$–$C_4$)-alkyl, nitro or cyano, and $R^3$ and $R^4$ each represents, independently of the other, hydrogen, halogen, cyano, OH, SH, $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, mono-$C_1$–$C_4$-alkylamino, di-$C_1$–$C_4$-alkylamino, $C_1$–$C_4$-alkoxycarbonyl or $C_1$–$C_4$-alkoxy-($C_1$–$C_4$)-alkyl, and to the salts and addition compounds thereof with acids, bases and complex formers.

Within the scope of the invention disclosed herein, the generic terms used include, for example, the following specific individual substituents, but this list does not imply any limitation of the invention:

Alkyl includes the straight-chained or branched $C_1$–$C_6$-alkyls, such as methyl, ethyl, n-propyl, isopropyl, n-butyl, sec.-butyl, tert.-butyl, isobutyl, the isomeric pentyls such as, for example, tert.-pentyl (1,1-dimethylpropyl), isopentyl (1-ethylpropyl), and also the isomeric hexyl radicals. $C_1$–$C_3$-alkyl radicals are preferred.

Halogen is fluorine, chlorine, bromine or iodine. Fluorine, chlorine and bromine are preferred.

Haloalkyl indicates alkyl radicals that are wholly or partially substituted by identical or different halogen atoms according to the respective definitions given, such as, for example, 2,2,2-trifluoroethyl, 1,1,1,3,3,3-hexafluoroprop-2-yl, trifluoromethyl or difluoromethyl.

As $C_1$–$C_4$-alkoxycarbonyl radicals there may be mentioned, inter alia, methoxycarbonyl, ethoxycarbonyl and also the isomeric propoxycarbonyls and butoxycarbonyls.

Alkoxy within the scope of the respective definition of the isomeric alkoxy radicals is especially methoxy or ethoxy.

Haloalkoxy and haloalkylthio within the scope of the respective definition are the isomeric alkyl radicals that are mono- or poly-substituted by identical or different halogen atoms, such as, for example, trifluoromethoxy, 2,2,2-trifluoroethoxy, trifluoromethylthio, 2,2,3,3,3-pentafluoropropoxy or 1,1,2,2-tetrafluoroethoxy.

Alkoxyalkyl radicals are, inter alia, 2-ethoxyethyl, 2-methoxyethyl, 3-methoxypropyl, 2-methoxy-1-methylethyl and methoxymethyl.

Di-$C_1$–$C_4$-alkylamino is a group substituted by identical or different alkyl radicals, such as dimethylamino, diethylamino and methylethylamino.

In the other substituents, which are composed of several basic components, the partial components can be freely selected within the respective definition given and have the above meanings.

Attention is drawn to compounds of the formula I in which
$R^1$ and $R^2$ each represents, independently of the other, hydrogen, halogen, $C_1$–$C_3$-alkyl, $C_1$–$C_3$-haloalkyl, $C_1$–$C_3$-alkoxy, $C_1$–$C_3$-alkoxycarbonyl, nitro, cyano or $C_1$–$C_3$-alkoxy-($C_1$–$C_3$)-alkyl, and $R^3$ and $R^4$ each represents, independently of the other, hydrogen, halogen, $C_1$–$C_3$-alkyl, $C_1$–$C_3$-haloalkyl, $C_1$–$C_4$-alkoxy, $C_1$–$C_3$-haloalkoxy, $C_1$–$C_4$-alkylthio, amino, mono-$C_1$–$C_3$-alkylamino, di-$C_1$–$C_3$-alkylamino, cyano, $C_1$–$C_4$-alkoxycarbonyl or $C_1$–$C_4$-alkoxy-($C_1$–$C_4$)-alkyl.

Preferred are compounds of the formula I in which
$R^1$ represents hydrogen, halogen, $C_1$–$C_3$-alkyl, $C_1$–$C_3$-haloalkyl, $C_1$–$C_3$-alkoxy or $C_1$–$C_3$-alkoxycarbonyl, $R^2$ represents hydrogen, halogen, $C_1$–$C_3$-alkyl, nitro or cyano, and $R^3$ and $R^4$ each represents, independently of the other, hydrogen, halogen, $C_1$–$C_3$-alkyl, $C_1$–$C_3$-haloalkyl, $C_1$–$C_4$-alkoxy, $C_1$–$C_3$-haloalkoxy, $C_1$–$C_4$-alkylthio, amino, mono-$C_1$–$C_3$-alkylamino, di-$C_1$–$C_3$-alkylamino, cyano, $C_1$–$C_4$-alkoxycarbonyl or $C_1$–$C_3$-alkoxy-($C_1$–$C_3$)-alkyl.

The invention relates especially to compounds of the formula I in which
$R^1$ represents hydrogen, chlorine, methyl, trifluoromethyl, methoxy or ethoxycarbonyl,
$R^2$ represents hydrogen, chlorine, methyl or nitro,
$R^3$ represents hydrogen, fluorine, chlorine, methyl, ethyl, propyl, trifluoromethyl, methoxy, ethoxy, difluoromethoxy, 1,1,2,2-tetrafluoroethoxy, dimethylamino, ethoxycarbonyl or $C_1$–$C_4$-alkylthio, and $R^4$ represents hydrogen, fluorine, chlorine, bromine, methyl, methoxymethyl, methoxyethyl, $C_1$–$C_4$-alkoxy, 1,1,2,2-tetrafluoroethoxy, dimethylamino, difluoromethoxy, fluoromethoxy, trifluoromethyl or $C_1$–$C_4$-alkylthio.

Especially preferred are compounds of the formula I in which
$R^1$ represents hydrogen, methyl, methoxy, trifluoromethyl or Cl,
$R^2$ represents hydrogen or methyl,
$R^3$ represents methyl, ethyl, propyl, chlorine, trifluoromethyl, 1,1,2,2-tetrafluoroethoxy, methylthio, propylthio, ethoxy or methoxy, and
$R^4$ represents fluorine, chlorine, methyl, methoxy, methoxymethyl, difluoromethoxy, fluoromethoxy, trifluoromethyl or bromine.

Regarding the position of the substituents $R^1$ and $R^2$, compounds of the formula I are preferred in which one or each of the substituents is bonded in the 5 or 6 position of the phenyl ring, as the case may be.

Also especially preferred are compounds of the formula I in which $R^1$ and $R^2$ represent hydrogen, $R^3$ represents methoxy or methyl and $R^4$ represents chlorine, methyl, methoxy, methoxymethyl, trifluoromethyl or difluoromethoxy.

The compounds of the formula I may be prepared as follows:

(a) an aniline of the formula II is reacted with phosgene to form a carbamine chloride of the formula III and, in a second stage, this is reacted with $NH_3$ to form a urea of the formula I

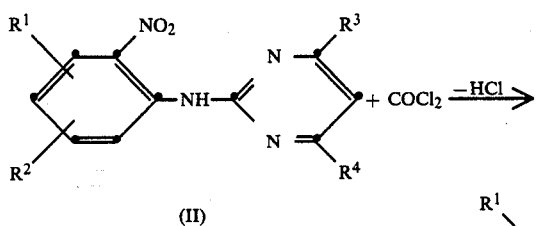

(II)

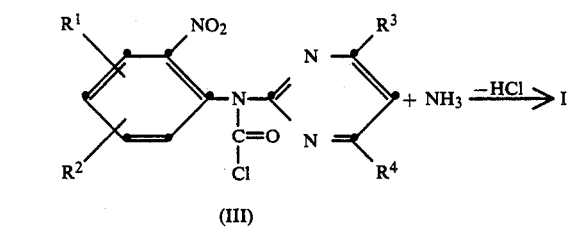

(III)

or (b) an aniline of the formula II is reacted with halosulphonyl isocyanate to form a halosulphonylurea of the formula IV and this is hydrolysed, in a second stage or directly, to form a compound of the formula I

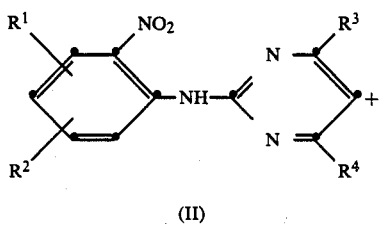

(II)

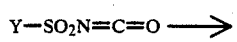

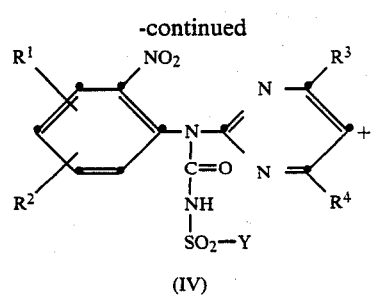

(IV)

$$2H_2O \xrightarrow[-SO_4H_2]{-HY} I,$$

Y is the above formulae representing a group that can be removed under the reaction conditions, such as halogen, preferably chlorine, or (c) a sulphonylurea of the formula V is rearranged under the action of an aqueous base to form a urea of the formula I

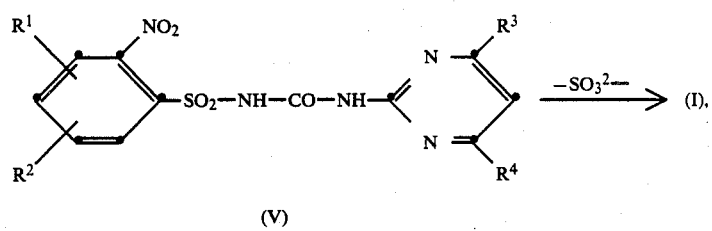

(V)

the aqueous base used preferably being NaOH/water or KOH/water.

The reactions II→III, III→I and IV→I, which proceed with the removal of hydrogen halide or the elimination of HY, are preferably carried out using acid-binding agents (bases).

Suitable acid-binding agents are organic or inorganic bases, for example tertiary amines such as trialkylamines (trimethylamine, triethylamine, tripropylamine etc.), pyridines, (pyridine, 4-dimethylaminopyridine, 4-pyrrolidylaminopyridine, etc.), and alcoholates such as, for example, potassium tert.-butoxide, sodium methoxide or ethoxide. The reactions mentioned above as well as reaction V→I can also be carried out with bases under phase transfer conditions according to processes known per se (lit. Dehmlow & Dehmlow, Phase Transfer Catalysis, Verlag Chemie, Weinheim, 1983).

In process variants (a) and (b), in principle one or more inert solvents or diluents may be present unless expressly specified individually. The following, for example, are suitable: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert.-butylmethyl ether etc.), anisole, dioxan, tetrahydrofuran; nitriles such as acetonitrile, propionitrile; N,N-dialkylated amides such as dimethylformamide; dimethyl sulphoxide; ketones such as acetone, diethyl ketone, methyl ethyl ketone; and mixtures of such solvents with each other.

Some of the 2-nitroanilines of the formula II are known from EP-A 172 786. Like the novel carbamoyl chlorides of the formula III and the novel ureas of the formula IV they are valuable intermediates for the synthesis of the herbicidally active ureas I.

The invention thus also relates to the novel compounds of the formula

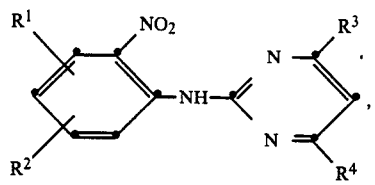

in which
R¹ and R² each represents, independently of the other, hydrogen, halogen, $C_1-C_6$-alkyl, $C_1-C_4$-haloalkyl, $C_1-C_4$-alkoxy, $C_1-C_4$-haloalkoxy, $C_1-C_4$-alkoxycarbonyl, $C_1-C_4$-alkoxy-$(C_1-C_4)$-alkyl, nitro or cyano, and R³ and R⁴ each represents, independently of the other, hydrogen, halogen, cyano, OH, SH, $C_1-C_6$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, amino, mono-$C_1-C_4$-alkylamino, di-$C_1-C_4$-alkylamino, $C_1-C_4$-alkoxycarbonyl or $C_1-C_4$-alkoxy-$(C_1-C_4)$-alkyl with the proviso that when R¹ represents 4-$NO_2$ and R² represents 6-$CF_3$ R³ and R⁴ do not represent F, Cl, Br, $C_1-C_4$-alkyl, $C_1-C_3$-alkoxy, $C_1-C_4$-alkylthio, cyano, $CCl_3$, $CF_3$, $OCH_2OC_2H_5$, $OCH_2F$, $CH_2OCH_3$ or $OCH_2CF_3$ and when R¹ represents 4-$CF_3$ and R² represents 6-$NO_2$ the following pairs of meanings for R³ and R⁴ are not included: Cl, Cl; n-$C_6H_{13}$, Cl; Br, Br; CN, $CH_3$; F, F; $CH_3$, $CH_3$; Cl, $SCH_3$; Cl, $OCH_3$; Cl, $OCH_2CF_3$; Cl, $CH_2Cl$ and Cl, $CH_2F$; and with the proviso that R¹ and R² do not each represent hydrogen when R³ and R⁴ each represents $CH_3$.

The invention relates furthermore to compounds of the formula

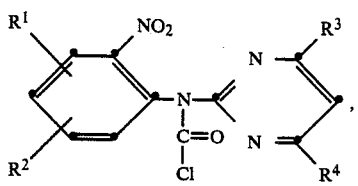

in which
R¹ and R² each represents, independently of the other, hydrogen, halogen, $C_1-C_6$-alkyl, $C_1-C_4$-haloalkyl, $C_1-C_4$-alkoxy, $C_1-C_4$-haloalkoxy, $C_1-C_4$-alkoxycarbonyl, $C_1-C_4$-alkoxy-$(C_1-C_4)$-alkyl, nitro or cyano, and R³ and R⁴ each represents, independently of the other, hydrogen, halogen, cyano, $C_1-C_6$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, amino, mono-$C_1-C_4$-alkylamino, di-$C_1-C_4$-alkylamino, $C_1-C_4$-alkoxycarbonyl or $C_1-C_4$-alkoxy-$(C_1-C_4)$-alkyl, and ureas of the formula

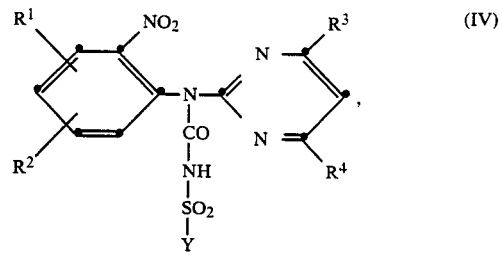

in which
R¹ and R² each represents, independently of the other, hydrogen, halogen, $C_1-C_6$-alkyl, $C_1-C_4$-haloalkyl, $C_1-C_4$-alkoxy, $C_1-C_4$-haloalkoxy, $C_1-C_4$-alkoxycarbonyl, $C_1-C_4$-alkoxy-$(C_1-C_4)$-alkyl, nitro or cyano, and R³ and R⁴ each represents, independently of the other, hydrogen, halogen, cyano, $C_1-C_6$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, amino, mono-$C_1-C_4$-alkylamino, di-$C_1-C_4$-alkylamino, $C_1-C_4$-alkoxycarbonyl or $C_1-C_4$-alkoxy-$(C_1-C_4)$-alkyl, and Y represents halogen, $C_1-C_4$-alkoxy or phenoxy.

The compounds of the formula III and IV are intermediates in processes (a) and (b) and can be prepared as described for those processes from the corresponding 2-nitroanilines of the formula II.

The novel 2-nitroanilines of the formula II can be prepared analogously to processes known in the literature, for example:

(aa) by reacting guanidines of the formula VI with 1,3-dicarbonyl compounds of the formula VII the condensation reaction if desired being carried out in the presence of water-binding agents (lit.: D. J. Brown in "The Chemistry of Heterocyclic Compounds" vol. VI 1962, Interscience Publ. New York) or (bb) by reacting a halobenzene of the formula VIII with a 2-aminopyrimidine of the formula IX

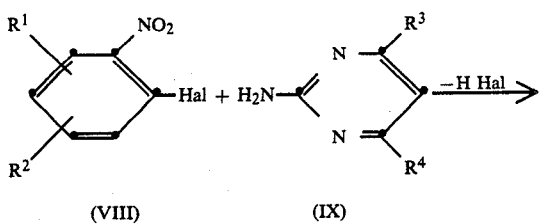

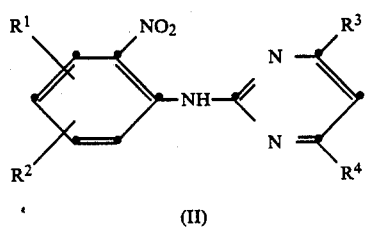

in which $R^1$ and $R^2$ are bonded preferably in the 4- and 6-position, respectively, of the phenyl system (in II) and represent an electron-attracting group (lit. EP-A-O 172 786), or (cc) by decomposing a sulphonylurea of the formula V at elevated temperature under the action of an aqueous base

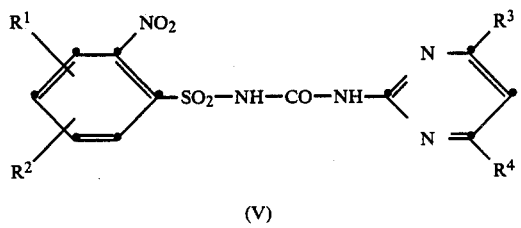 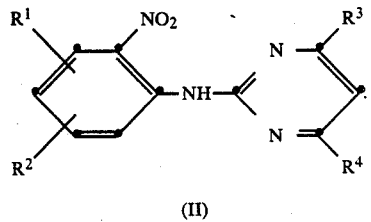

The invention relates also to herbicidal and plant growth-regulating compositions containing a compound of the formula I together with suitable adjuvants and/or carriers.

The active ingredients of the formula I are in general used successfully at application rates of from 0.005 to 5 kg/ha, especially from 0.1 to 3 kg/ha. The dosage necessary to achieve the desired action can be acertained by tests. It is dependent upon the nature of the action, the stage of development of the crop plants and of the weed and the application (locus, time, method) and may vary within wide ranges determined by these parameters.

At low rates of application the compounds of the formula I are distinguished by growth-inhibiting and herbicidal properties which make them excellent for use in crops of useful plants, especially cereals, cotton, soya, maize and rice.

The compounds of formula I also have plant growth-regulating properties. The growth of both monocotyledons and dicotyledons is affected.

Inhibition of the vegetative growth makes it possible with many crop plants for the crop to be more densely planted, so that it is possible to achieve a higher yield per unit area of soil.

Another mechanism of the increase in yield when using growth regulators is based on the fact that the nutrients are used to the greater advantage of the formation of the flowers and fruit whilst the vegetative growth is restricted.

If the rates of application are higher, weeds and grasses are damaged in their development to such an extent that they die.

The invention relates also to herbicidal and plant growth-regulating compositions that contain an active ingredient of the formula I, and to methods of controlling weeds pre-emergence and post-emergence and of influencing the growth of monocotyledons and dicotyledons, especially grasses, tropical cover crops and side shoots.

The compounds of the formula I are used in unmodified form or, preferably, in the form of compositions together with adjuvants customary in the art of formulation and are therefore processed in known manner, for example into emulsifiable concentrates, directly sprayable or dilutable solutions, dilute emulsions, wettable powders, soluble powders, dusts, granulates, and encapsulations in, for example, polymeric substances. As with the nature of the compositions, the methods of application, such as spraying, atomizing, dusting, scattering or pouring, are chosen in accordance with the intended objectives and the prevailing circumstances.

The formulations, that is to say the compositions, preparations or formulations containing the active ingredient of the formula I and, where appropriate, a solid or liquid adjuvant, are prepared in known manner, for example by intimate mixing and/or grinding of the active ingredients with extenders, such as, for example, solvents, solid carriers and, where appropriate, surface-active compounds (surfactants).

Suitable solvents are: aromatic hydrocarbons, preferably the fractions $C_8$–$C_{12}$, such as, for example, xylene mixtures or substituted naphthalenes, phthalic acid esters such as dibutyl or dioctyl phthalate, aliphatic hydrocarbons such as cyclohexane or paraffins, alcohols and glycols and ethers and esters thereof, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, and also vegetable oils which may be epoxidised, such as epoxidised coconut oil or soybean oil, or water.

The solid carriers used, for example for dusts and dispersible powders, are normally powdered natural minerals, such as calcite, talcum, kaolin, montmorillonite or attapulgite. In order to improve the physical properties is it also possible to add highly dispersed silicic acid or highly dispersed absorbent polymers. Suitable granulated adsorptive carriers are porous types such as, for example, pumice, broken brick, sepiolite or bentonite, and suitable non-sorbent carrier materials are, for example, calcite or sand. Furthermore, a large number of pre-granulated materials of inorganic or organic nature can be used such as, especially, dolomite or pulverised plant residues.

Depending upon the nature of the active ingredient of the formula I to be formulated, suitable surface-active compounds are non-ionic, cationic and/or anionic surfactants having good emulsifying, dispersing and wetting properties. The term surfactants is also to include mixtures of surfactants.

Suitable anionic surfactants can be either so-called water-soluble soaps or water-soluble synthetic surface-active compounds.

As soaps there may be mentioned alkali metal, alkaline earth metal or substituted or unsubstituted ammonium salts of higher fatty acids ($C_{10}$–$C_{22}$) such as, for example, the sodium or potassium salts of oleic or stearic acid, or of mixtures of natural fatty acids that can be obtained, for example, from coconut oil or tallow oil. Fatty acid methyltaurin salts should also be mentioned.

More frequently, however, so-called synthetic surfactants are used, especially fatty sulphonates, fatty sulphates, sulphonated benzimidazole derivatives or alkylarylsulphonates.

The fatty sulphonates or sulphates are generally in the form of alkali metal, alkaline earth metal or substituted or unsubstituted ammonium salts and contain an alkyl radical having from 8 to 22 carbon atoms, alkyl also including the alkyl moiety of acyl radicals, for example the sodium or calcium salt of lignosulphonic acid, of dodecylsulphuric acid ester or of a mixture of fatty alcohol sulphates produced from natural fatty acids. Also included are the salts of sulphuric acid esters and sulphonic acids of fatty alcohol/ethylene oxide adducts. The sulphonated benzimidazole derivatives preferably contain 2 sulphonic acid groups and a fatty acid radical having from 8 to 22 carbon atoms. Alkylarylsulphonates are, for example, the sodium, calcium or triethanolamine salts of dodecylbenzenesulphonic acid, of dibutylnaphthalenesulphonic acid or of a naphthalenesulphonic acid/formaldehyde condensation product.

There also come into consideration corresponding phosphates such as, for example, salts of the phosphoric acid ester of an adduct of p-nonylphenol with from 4 to 14 mols of ethylene oxide, or phospholipids.

Non-ionic surfactants are especially polyglycol ether derivatives of aliphatic or cycloaliphatic alcohols, of saturated or unsaturated fatty acids and alkylphenols, which derivatives may contain from 3 to 10 glycol ether groups and from 8 to 20 carbon atoms in the (aliphatic) hydrocarbon moiety and from 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The compounds mentioned usually contain from 1 to 5 ethylene glycol units per propylene glycol unit.

There may be mentioned as examples of non-ionic surfactants nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, also come into consideration.

The cationic surfactants are especially quaternary ammonium salts that contain, as N-substituent, at least one alkyl radical having from 8 to 22 carbon atoms and, as further substituents, lower, optionally halogenated alkyl, benzyl or lower hydroxyalkyl radicals. The salts are preferably in the form of halides, methyl sulphates or ethyl sulphates, for example stearyltrimethylammonium chloride or benzyldi-(2-chloroethyl)-ethylammonium bromide.

The surfactants customarily employed in the art of formulation are described, inter alia, in the following publications:

"McCutcheon's Detergents and Emulsifiers Annual" MC Publishing Corp., Ridgewood, N.J., 1979. Dr. Helmut Stache "Tensid Taschenbuch" Carl Hanser Verlag, Munich/Vienna 1981.

The preparations generally contain from 0.1 to 95%, especially from 0.1 to 80%, of active ingredient of the formula I, from 1 to 99.9% of a solid or liquid adjuvant and from 0 to 25%, especially from 0.1 to 25%, of a surfactant.

Preferred formulations have especially the following compositions: (%=percent by weight)

| Emulsifiable concentrates: | |
|---|---|
| active ingredient of formula I: | 1 to 20%, preferably 5 to 10% |
| surfactant: | 5 to 30%, preferably 10 to 20% |
| liquid carrier: | 50 to 94%, preferably 70 to 85%. |
| Dusts: | |
| active ingredient of formula I: | 0.1 to 10%, preferably 0.1 to 1% |
| solid carrier: | 99.9 to 90%, preferably 99.9 to 99% |
| Suspension concentrates: | |
| active ingredient of formula I: | 5 to 75%, preferably 10 to 50% |
| water: | 94 to 25%, preferably 90 to 30% |
| surfactant: | 1 to 40%, preferably 2 to 30%. |
| Wettable powders: | |
| active ingredient of formula I: | 0.5 to 90%, preferably 1 to 80% |
| surfactant: | 0.5 to 20%, preferably 1 to 15% |
| solid carrier: | 5 to 95%, preferably 15 to 90%. |
| Granulates: | |
| active ingredient of formula I: | 0.5 to 30%, preferably 3 to 15% |
| solid carrier: | 99.5 to 70%, preferably 97 to 85%. |

Whereas concentrated compositions are preferred as commercial products, the end user will as a rule use dilute formulations. The formulations can be diluted to a concentration as low as 0.001% active ingredient. The rates of application are normally from 0.005 to 5 kg active ingredient/ha.

The compositions may also contain further additives such as stabilisers, antifoams, viscosity regulators, binders, tackifiers and also fertilisers or other active ingredients for achieving special effects.

PREPARATION EXAMPLES

The (uncorrected) melting points in the following Preparation Examples are in °C.

H.1.1. Synthesis of N-(6-chloro-4-methylpyrimidin-2-yl)-N-2-nitrophenylurea 79.3 g (0.3 mol) of N-(6-chloro-4-methylpyrimidin-2-yl)-2-nitroaniline are dissolved in 2.2 l of ethyl acetate at 60°. The solution is cooled to 5° whereupon yellow crystals precipitate. 56.6 g (0.4 mol) of chlorosulphonyl isocyanate are added thereto and then the whole is stirred for 15 minutes at 5°. Subsequently, 300 ml of cold water are added and the organic phase is separated off, dried with sodium sulphate and concentrated by evaporation. The solid residue is triturated with a little ethyl acetate.

71.5 g (74.4%) of the title compound of formula

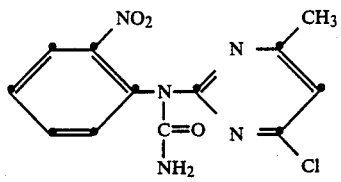

(compound No. 1.007) are isolated in the form of crystals having a melting point of 155° C.

H.1.2. Synthesis of N-(6-chloro-4-methylpyrimidin-2-yl)-N-2-nitrophenylurea 18.6 g (0.05 mol) of 3-(6-chloro-4-methylpyrimidin-2-yl)-1-(2-nitrophenylsulphonyl)-urea are suspended in 100 ml of water and 200 ml of chloroform. A solution of 3.2 g of sodium hydroxide in 350 ml of water is then added dropwise at 25° within a period of 4 hours. The 2-phase solution is stirred for 16 hours. The CHCl$_3$ phase is then separated off, dried with sodium sulphate and concentrated by evaporation. The residue is recrystallised from chloroform.

3.3 g (21.4%) of the title compound of formula

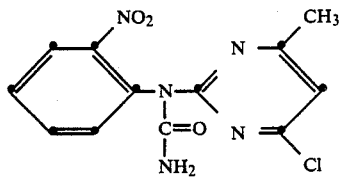

(compound No. 1.007) are isolated in the form of crystals haaving a melting point of 155° C.

The compounds of formula

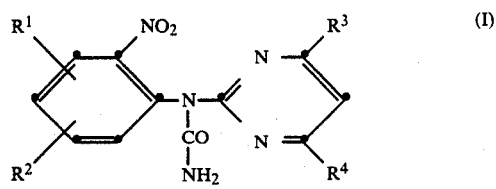

listed in the following Table 1 are prepared analogously to the H.1. Preparation Examples:

TABLE 1

| Comp. No. | R$^1$ | R$^2$ | R$^3$ | R$^4$ | physical data |
|---|---|---|---|---|---|
| 1.001 | H | H | OCH$_3$ | OCH$_3$ | m.p. 157–158° |
| 1.002 | H | H | CH$_3$ | CH$_3$ | from 150°, decomp. |
| 1.003 | H | H | OCH$_3$ | CH$_2$OCH$_3$ | m.p. 124–125° |
| 1.004 | H | H | OCH$_3$ | CH$_3$ | m.p. 153–154° |
| 1.005 | H | H | CH$_3$ | OCHF$_2$ | m.p. 144°, decomp. |
| 1.006 | H | H | OCH$_3$ | Cl | m.p. 172–175° |
| 1.007 | H | H | CH$_3$ | Cl | m.p. 155° |
| 1.008 | 4-Cl | H | CH$_3$ | CH$_3$ | m.p. 156°, decomp. |
| 1.009 | H | H | CH$_3$ | F | m.p. 134–135° |
| 1.010 | H | H | CH$_2$CH$_3$ | Cl | m.p. 136–137° |
| 1.011 | H | H | CH$_2$CH$_3$ | OCHF$_2$ | m.p. 132–134° |
| 1.012 | H | H | CH$_3$ | Br | m.p. 174–175° |
| 1.013 | H | H | Cl | Cl | m.p. 164–165° |
| 1.014 | H | H | F | F | |
| 1.015 | H | H | Cl | OCHF$_2$ | |
| 1.016 | H | H | OCHF$_2$ | OCHF$_2$ | |
| 1.017 | H | H | OCH$_2$CH$_3$ | CH$_3$ | m.p. 142–144° |
| 1.018 | H | H | SCH$_3$ | CH$_3$ | m.p. 180–182° |
| 1.019 | H | H | SCH(CH$_3$)$_2$ | CH$_3$ | m.p. 151–152° |
| 1.020 | H | H | SCH$_3$ | Cl | m.p. 133–135° |
| 1.021 | H | H | SC$_4$H$_9$(n) | Cl | |
| 1.022 | H | H | COOEt | Cl | |
| 1.023 | H | H | COOEt | CH$_3$ | |
| 1.024 | H | H | SCH$_2$CH$_3$ | OCHF$_2$ | |
| 1.025 | H | H | CF$_3$ | Cl | from 135°, decomp. |
| 1.026 | H | H | CF$_3$ | F | |
| 1.027 | H | H | CF$_3$ | OCH$_2$CH$_3$ | |
| 1.028 | H | H | CF$_3$ | SCH$_3$ | |
| 1.029 | H | H | CF$_3$ | N(CH$_3$)$_2$ | |
| 1.030 | H | H | N(CH$_3$)$_2$ | Cl | |
| 1.031 | H | H | N(CH$_3$)$_2$ | CH$_3$ | |
| 1.032 | H | H | OCF$_2$CHF$_2$ | CH$_3$ | m.p. 137–138° |
| 1.033 | H | H | OCF$_2$CHF$_2$ | OCF$_2$CHF$_2$ | |
| 1.034 | 4-CH$_3$ | H | CH$_3$ | Cl | m.p. 159–160° |
| 1.035 | 4-CH$_3$ | H | CH$_3$ | OCHF$_2$ | |
| 1.036 | 4-CH$_3$ | H | CH$_3$ | F | |
| 1.037 | 4-CH$_3$ | H | CH$_3$ | OCF$_2$CHF$_2$ | |
| 1.038 | 4-CH$_3$ | H | CH$_3$ | SCH$_3$ | |
| 1.039 | 4-CF$_3$ | H | CH$_3$ | Cl | |
| 1.040 | 4-CF$_3$ | H | Cl | Cl | |
| 1.041 | 4-CF$_3$ | H | OCH$_3$ | CH$_2$OCH$_3$ | |
| 1.042 | 4-CF$_3$ | H | CH$_3$ | H | |
| 1.043 | 4-CF$_3$ | H | H | H | |
| 1.044 | 4-Cl | H | CH$_3$ | Cl | m.p. 149–150° |
| 1.045 | 4-Cl | H | CH$_3$ | F | |
| 1.046 | 4-Cl | H | CH$_3$ | OCHF$_2$ | m.p. 128–129° |
| 1.047 | 4-Cl | H | CH$_3$ | SCH$_2$CH$_3$ | |
| 1.048 | 4-COOEt | H | CH$_3$ | CH$_3$ | |

TABLE 1-continued

| Comp. No. | R¹ | R² | R³ | R⁴ | physical data |
|---|---|---|---|---|---|
| 1.049 | 4-COOEt | H | $CH_3$ | Cl | |
| 1.050 | 4-COOEt | H | $CH_3$ | $OCH_3$ | |
| 1.051 | H | 6-$CH_3$ | $CH_3$ | Cl | m.p. 160–161° |
| 1.052 | H | 6-$CH_3$ | Cl | Cl | |
| 1.053 | H | 6-$CH_3$ | Cl | $SCH_3$ | |
| 1.054 | 4-$OCH_3$ | H | $CH_3$ | Cl | |
| 1.055 | 4-$OCH_3$ | H | $CH_3$ | $CH_3$ | |
| 1.056 | 5-$CH_3$ | H | $CH_3$ | $CH_3$ | |
| 1.057 | 5-$CH_3$ | H | $CH_3$ | $OCHF_2$ | |
| 1.058 | 5-$CH_3$ | H | $CH_3$ | Cl | |
| 1.059 | 5-$CH_3$ | H | $CH_3$ | $OCF_2CHF_2$ | |
| 1.060 | 4-Cl | 6-Cl | $CH_3$ | $CH_3$ | |
| 1.061 | 4-Cl | 6-Cl | $CH_3$ | Cl | |
| 1.062 | 4-Cl | 6-Cl | Cl | Cl | |
| 1.063 | 4-Cl | 6-Cl | $CH_3$ | F | |
| 1.064 | 4-Cl | 6-Cl | Cl | $SC_2H_5$ | |
| 1.065 | 4-$CF_3$ | 6-$NO_2$ | $CH_3$ | Cl | |
| 1.066 | 4-$CF_3$ | 6-$NO_2$ | H | H | |
| 1.067 | 4-$CF_3$ | 6-$NO_2$ | $CH_3$ | H | |
| 1.068 | 4-$CF_3$ | 6-$NO_2$ | $CH_3$ | $OCHF_2$ | |
| 1.069 | 4-$CF_3$ | 6-$NO_2$ | $CH_3$ | $CH_2OCH_3$ | |
| 1.070 | 4-$CF_3$ | 6-$NO_2$ | $CH_3$ | $CH_3$ | |
| 1.071 | H | H | $C_3H_7(n)$ | Cl | m.p. 145–147° decomp. |
| 1.072 | H | H | $C_3H_7(n)$ | $OCH_2F$ | m.p. 117–118° |
| 1.073 | H | H | $CF_3$ | Br | m.p. 154–155° |
| 1.074 | 4-Cl | H | $CF_3$ | Cl | m.p. 135–138° |
| 1.075 | 4-Cl | H | $CF_3$ | $OCHF_2$ | m.p. 145–150° |
| 1.076 | 4-$CF_3$ | H | $CH_3$ | $OCH_3$ | m.p. 159–160° |
| 1.077 | H | H | $CH_3$ | H | m.p. 143–144° |
| 1.078 | 4-$OCH_3$ | H | $CH_3$ | Cl | m.p. 164–165° |
| 1.079 | 4-Cl | H | $CH_3$ | Br | m.p. 180–182° |
| 1.080 | H | H | $CH_3$ | $CF_3$ | m.p. 140–141° |
| 1.081 | 5-Cl | H | $CH_3$ | Cl | m.p. 147–148° |
| 1.082 | H | 6-$CH_3$ | $CH_3$ | $CF_3$ | m.p. 174–175° |
| 1.083 | H | H | $CF_3$ | $CF_3$ | m.p. 168–171° |
| 1.084 | 5-Cl | H | $CH_3$ | $CF_3$ | |
| 1.085 | H | H | $CF_3$ | $OCH_3$ | m.p. 156–158° |
| 1.086 | H | H | $CF_3$ | $OC_4H_9(n)$ | m.p. 106–107° |
| 1.087 | H | H | $CF_3$ | $SCH(CH_3)_2$ | |
| 1.088 | H | H | $CF_3$ | $SC_2H_5$ | |
| 1.089 | H | H | $CF_3$ | $SC_4H_9(n)$ | |
| 1.090 | H | H | $CF_3$ | $OCH_2CH_2OCH_3$ | |
| 1.091 | H | H | $CF_3$ | $OC_3H_7(n)$ | |
| 1.092 | H | H | $CF_3$ | $OCF_2CHF_2$ | |
| 1.093 | H | 6-$CH_3$ | $CF_3$ | $OCH_3$ | |
| 1.094 | H | 6-$CH_3$ | $CF_3$ | $OC_2H_5$ | |
| 1.095 | H | 6-$CH_3$ | $CF_3$ | $OC_3H_7(n)$ | |
| 1.096 | H | 6-$CH_3$ | $CF_3$ | $OC_4H_9(iso)$ | |
| 1.097 | H | 6-$CH_3$ | $CF_3$ | $SCH_3$ | |
| 1.098 | H | 6-$CH_3$ | $CF_3$ | $SCH(CH_3)_2$ | |
| 1.099 | H | 6-$CH_3$ | $CF_3$ | $SC_4H_9(n)$ | |
| 1.100 | H | 6-Cl | $CH_3$ | Cl | |
| 1.101 | H | 6-Cl | $CH_3$ | $CF_3$ | |
| 1.102 | H | 6-Cl | $CF_3$ | $OCH_3$ | |
| 1.103 | H | 6-Cl | $CF_3$ | $OC_2H_5$ | |
| 1.104 | H | 6-Cl | $CF_3$ | $SCH_3$ | |
| 1.105 | H | 6-Cl | $CF_3$ | $SC_2H_5$ | |

H. 2.1. Synthesis of N-(6-chloro-4-methylpyrimidin-2-yl)-2-nitroaniline 24 g (0.064 mol) of 3-(6-chloro-4-methylpyrimidin-2-yl)-1-(2-nitrophenylsulphonyl)-urea are suspended in 150 ml of water and 200 ml of chloroform. After the addition of 25 ml of 30% sodium hydroxide solution, the reaction mixture is stirred for 1 hour at 50°–55°, and the chloroform phase is separated off and dried with sodium sulphate. After the chlofoorm has been evaporated off, 14.7 g (86.7% of the theoretical amount) of the title compound of formula

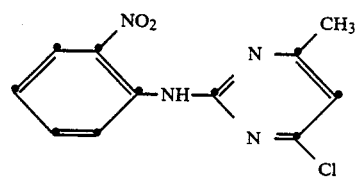

(compound No. 2.007) are obtained in the form of crystals having a melting point of 175° C.

H. 2.2 Synthesis of N-(6-chloro-4-methylpyrimidin-2-yl)-2-nitroaniline

A mixture of 160 g (0.65 mol) of N-(6-hydroxy-4-methylpyrimidin-2-yl)-o-nitroaniline, 2 ml of N,N-dimethylformamide and 120 ml of phosphorus oxychloride are heated at reflux for 3 hours. After having been cooled, and black slurry is dissolved in chloroform and this solution is added dropwise to 1 l of water. The temperature is maintained at 35° by the addition of ice. After 1 hour the organic phase is separated off and the aqueous phase is washed with chloroform. The two chloroform solutions are together dried and concentrated by evaporation. The black residue is dissolved in hot toluene, filtered and crystallised by the addition of hexane. 104.9 g (61%) of the title compound of formula

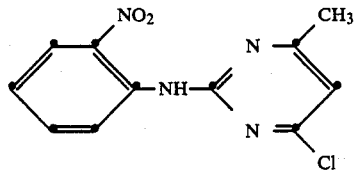

(compound No. 2.007) are obtained in the form of crystals having a melting point of 175° C.

H. 2.3. Synthesis of N-(6-hydroxy-4-methylpyrimidin-2-yl)-2-nitroaniline 121 g (0.5 mol) of 2-nitrophenyl-guanidine-carbonate, 100 g of ethyl acetoacetate and 200 ml of diethylene glycol dimethyl ether are heated first to 65° and, when the evolution of $CO_2$ has ceased, to 140°. In the course of this ethanol and water are distilled off. After 3½ hours the suspension is cooled, water is added and the pH is adjusted to 4–5 with concentrated hydrochloric acid. The yellow precipitate is filtered off, washed with water and dried in vacuo at 80° C. 80.3 g (65.2% of the theoretical amount) of the title compound of formula

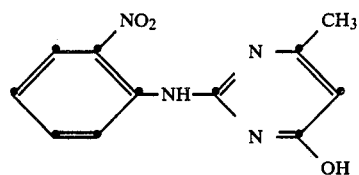

(compound No. 2.071) are obtained in the form of crystals having a melting point of 240°–242°.

The compounds of formula

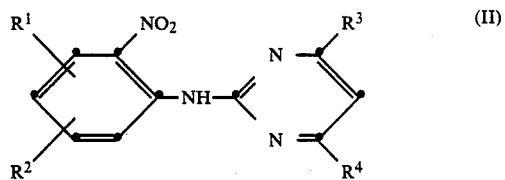

listed in the following Table 2 can be prepared analogously in the H.2. Preparation Examples:

TABLE 2

| Comp. No. | $R^1$ | $R^2$ | $R^3$ | $R^4$ | physical data |
|---|---|---|---|---|---|
| 2.001 | H | H | OCH3 | OCH3 | m.p. 174–175° |
| 2.002 | H | H | CH3 | CH3 | m.p. 163–164° |
| 2.003 | H | H | OCH3 | CH2OCH3 | m.p. 121–123° |
| 2.004 | H | H | OCH3 | CH3 | m.p. 144–145° |
| 2.005 | H | H | CH3 | OCHF2 | m.p. 104° |
| 2.006 | H | H | OCH3 | Cl | m.p. 160° |
| 2.007 | H | H | CH3 | Cl | m.p. 175° |
| 2.008 | H | H | CH3 | F | m.p. 126–130° |
| 2.009 | H | H | CH2CH3 | Cl | m.p. 89–90° |
| 2.010 | H | H | CH2CH3 | OCHF2 | m.p. 117–119° |
| 2.011 | 4-Cl | H | CH3 | CH3 | |
| 2.012 | H | H | CH3 | Br | m.p. 170–171° |
| 2.013 | H | H | Cl | Cl | m.p. 195–196° |
| 2.014 | H | H | F | F | |
| 2.015 | H | H | Cl | OCHF2 | |
| 2.016 | H | H | OCHF2 | OCHF2 | |
| 2.017 | H | H | OCH2CH3 | CH3 | m.p. 104–105° |
| 2.018 | H | H | SCH3 | CH3 | m.p. 180–182° |
| 2.019 | H | H | SCH(CH3)2 | CH3 | m.p. 75–77° |
| 2.020 | H | H | SCH3 | Cl | m.p. 153–155° |
| 2.021 | H | H | SC4H9(n) | Cl | |
| 2.022 | H | H | COOEt | Cl | |
| 2.023 | H | H | COOEt | CH3 | |
| 2.024 | H | H | SCH2CH3 | OCHF2 | |
| 2.025 | H | H | CF3 | Cl | m.p. 134° |
| 2.026 | H | H | CF3 | F | |
| 2.027 | H | H | CF3 | OCH2CH3 | |
| 2.028 | H | H | CF3 | SCH3 | |
| 2.029 | H | H | CF3 | N(CH3)2 | |
| 2.030 | H | H | N(CH3)2 | Cl | m.p. 175–176° |
| 2.031 | H | H | N(CH3)2 | CH3 | m.p. 123–124° |
| 2.032 | H | H | OCF2CHF2 | CH3 | m.p. 82–83° |
| 2.033 | H | H | OCF2CHF2 | OCF2CHF2 | |
| 2.034 | 4-CH3 | H | CH3 | Cl | m.p. 147–148° |
| 2.035 | 4-CH3 | H | CH3 | OCHF2 | |
| 2.036 | 4-CH3 | H | CH3 | F | |
| 2.037 | 4-CH3 | H | CH3 | OCF2CHF2 | |
| 2.038 | 4-CH3 | H | CH3 | SCH3 | |
| 2.039 | 4-CF3 | H | CH3 | Cl | m.p. 135–140° |
| 2.040 | 4-CF3 | H | Cl | Cl | |
| 2.041 | 4-CF3 | H | OCH3 | CH2OCH3 | |
| 2.042 | 4-CF3 | H | CH3 | H | |
| 2.043 | 4-CF3 | H | H | H | |
| 2.044 | 4-Cl | H | CH3 | Cl | m.p. 152–155° |
| 2.045 | 4-Cl | H | CH3 | F | |

TABLE 2-continued

| Comp. No. | R¹ | R² | R³ | R⁴ | physical data |
|---|---|---|---|---|---|
| 2.046 | 4-Cl | H | CH₃ | OCHF₂ | |
| 2.047 | 4-Cl | H | CH₃ | SCH₂CH₃ | m.p. 118–122° |
| 2.048 | 4-COOEt | H | CH₃ | CH₃ | |
| 2.049 | 4-COOEt | H | CH₃ | Cl | |
| 2.050 | 4-COOEt | H | CH₃ | OCH₃ | |
| 2.051 | H | 6-CH₃ | CH₃ | Cl | m.p. 149–150° |
| 2.052 | H | 6-CH₃ | Cl | Cl | |
| 2.053 | H | 6-CH₃ | Cl | SCH₃ | |
| 2.054 | 4-OCH₃ | H | CH₃ | Cl | m.p. 137–138° |
| 2.055 | 4-OCH₃ | H | CH₃ | CH₃ | |
| 2.056 | 5-CH₃ | H | CH₃ | CH₃ | |
| 2.057 | 5-CH₃ | H | CH₃ | OCHF₂ | |
| 2.058 | 5-CH₃ | H | CH₃ | Cl | |
| 2.059 | 5-CH₃ | H | CH₃ | OCF₂CHF₂ | |
| 2.060 | 4-Cl | 6-Cl | CH₃ | CH₃ | |
| 2.061 | 4-Cl | 6-Cl | CH₃ | Cl | |
| 2.062 | 4-Cl | 6-Cl | Cl | Cl | |
| 2.063 | 4-Cl | 6-Cl | CH₃ | F | |
| 2.064 | 4-Cl | 6-Cl | Cl | SC₂H₅ | |
| 2.065 | 4-CF₃ | 6-NO₂ | CH₃ | Cl | m.p. 143–145° |
| 2.066 | 4-CF₃ | 6-NO₂ | H | H | |
| 2.067 | 4-CF₃ | 6-NO₂ | CH₃ | H | |
| 2.068 | 4-CF₃ | 6-NO₂ | CH₃ | OCHF₂ | |
| 2.069 | 4-CF₃ | 6-NO₂ | CH₃ | CH₂OCH₃ | |
| 2.070 | H | H | OH | OH | m.p. 150–155° |
| 2.071 | H | H | OH | CH₃ | m.p. 240–242° |
| 2.072 | H | H | OH | CH₂CH₃ | m.p. 217–221° |
| 2.073 | 4-CH₃ | H | OH | CH₃ | m.p. 229–231° |
| 2.074 | 4-Cl | H | OH | CH₃ | m.p. 245–248° |
| 2.075 | H | 6-CH₃ | OH | CH₃ | |
| 2.076 | H | H | OH | CF₃ | m.p. 249–251° |
| 2.077 | H | 6-CH₃ | OH | OH | |
| 2.078 | 4-OCH₃ | H | OH | CH₃ | m.p. 225–227° |
| 2.079 | 5-CH₃ | H | OH | CH₃ | |
| 2.080 | 4-Cl | 6-Cl | OH | OH | |
| 2.082 | 4-Cl | 6-Cl | OH | CH₃ | |
| 2.083 | H | H | C₃H₇(n) | Cl | m.p. 75–76° |
| 2.084 | H | H | C₃H₇(n) | OCHF₂ | m.p. 108–112° |
| 2.085 | 4-Cl | H | CF₃ | Cl | m.p. 102–104° |
| 2.086 | 4-Cl | H | CF₃ | OH | m.p. 242–245° |
| 2.087 | H | H | CF₃ | Br | m.p. 124–125° |
| 2.088 | 4-Cl | H | CH₃ | Br | m.p. 177–178° |
| 2.089 | H | H | CH₃ | H | m.p. 117–120° |
| 2.090 | 4-CF₃ | H | CH₃ | CH₃ | m.p. 136–139° |
| 2.091 | 4-CF₃ | H | CH₃ | OCH₃ | m.p. 120–123° |
| 2.092 | H | H | CH₃ | CF₃ | m.p. 121–123° |
| 2.093 | 5-Cl | H | CH₃ | OH | m.p. 225–228° |
| 2.094 | 5-Cl | H | CH₃ | Cl | m.p. 135–137° |
| 2.095 | H | H | CF₃ | CF₃ | m.p. 110–113° |
| 2.096 | H | 6-CH₃ | CH₃ | CF₃ | m.p. 118–120° |
| 2.097 | H | H | CF₃ | OCH₃ | m.p. 123–125° |
| 2.098 | H | H | CF₃ | OC₄H₉(n) | m.p. 70–71° |
| 2.099 | H | 6-CH₃ | CF₃ | OH | |
| 2.100 | H | 6-CH₃ | CF₃ | Cl | |
| 2.101 | H | 6-CH₃ | CF₃ | OCH₃ | |
| 2.102 | H | 6-CH₃ | CF₃ | OC₂H₅ | |
| 2.103 | H | 6-CH₃ | CF₃ | OC₃H₇(n) | |
| 2.104 | H | 6-CH₃ | CF₃ | OC₄H₉(iso) | |
| 2.105 | H | 6-CH₃ | CF₃ | SCH₃ | |
| 2.106 | H | 6-CH₃ | CF₃ | SCH(CH₃)₂ | |
| 2.107 | H | 6-CH₃ | CF₃ | SC₄H₉(n) | |
| 2.108 | H | 6-Cl | CH₃ | OH | |
| 2.109 | H | 6-Cl | CH₃ | Cl | |
| 2.110 | H | 6-Cl | CH₃ | CF₃ | |
| 2.111 | H | 6-Cl | CF₃ | OH | |
| 2.112 | H | 6-Cl | CF₃ | Cl | |
| 2.113 | H | 6-Cl | CF₃ | OCH₃ | |
| 2.114 | H | 6-Cl | CF₃ | OC₂H₅ | |
| 2.115 | H | 6-Cl | CF₃ | SCH₃ | |
| 2.116 | H | 6-Cl | CF₃ | SC₂H₅ | |

BIOLOGICAL EXAMPLES

EXAMPLE B1

Pre-emergence herbicidal action

In a greenhouse, immediately after sowing the test plants in seed trays, the surface of the soil is treated with an aqueous spray liquor corresponding to a rate of application of 4 kg of active ingredient/hectare. The seed trays are kept in a greenhouse at 22°–25° C. and 50–70% relative humidity.

After 3 weeks the herbicidal action is assessed in comparison with an untreated control group using a nine-stage evaluation scale (1=total damage, 9=no effect).

Evaluation figures of 1 to 4 (especially 1 to 3) indicate a good to very good herbicidal action. Evaluation figures of 6 to 9 (especially 7 to 9) indicate a good tolerance (especially in the case of crop plants).

In this test the compounds of Table 1 exhibit a pronounced herbicidal action.

In detail, for Setaria and Stellaria, at application rates of 4 kg/ha the following values are obtained:

| Compound No. | Setaria | Stellaria |
| --- | --- | --- |
| 1.001 | 3 | 2 |
| 1.002 | 2 | 1 |
| 1.004 | 2 | 2 |
| 1.005 | 2 | 2 |
| 1.006 | 1 | 2 |
| 1.007 | 1 | 2 |

EXAMPLE B2

Post-emergence herbicidal action (contact herbicide)

A number of weeds, both monocots and dicots, were sprayed after emergence (at the 4- to 6-leaf stage) with an aqueous dispersion of active ingredient at a rate of 4 kg of active ingredient per hectare and kept at 24°–26° C. and 45–60% relative humidity. 15 days after the treatment the test is evaluated. In this test also, the compounds of Table 1 exhibit good herbicidal action.

EXAMPLE B3

Herbicidal action for paddy

The water weeds *Echinochloa crus galli* and *Monocharia vag.* are sown in plastics beakers (60 cm² surface area, 500 ml volume). After sowing, the beakers are filled to the soil surface with water. 3 days after sowing, the water level is raised to slightly above (3–5 mm) the surface of the soil. Application is carried out 3 days after sowing by spraying the test substances onto the vessels. The dose which is used corresponds to a quantity of active ingredient of 4 kg per hectare. The plant beakers are then placed in a greenhouse under optimum growth conditions for the rice weeds, i.e. at 25°–30° C. and high humidity.

The tests are evaluated 3 weeks after the application. The compounds of Table 1 damage the weeds but not the rice.

EXAMPLE B4

Growth inhibition in tropical cover crops

The test plants (*Centrosema plumieri* and *Centrosema pubescens*) are raised until fully grown and cut back to a height of 60 cm. After 7 days, the active ingredient is sprayed on in the form of an aqueous emulsion. The test plants are kept at 70% relative humidity and 6000 lux artificial light for 14 hours each day and at a day temperature of 27° and a night temperature of 21° C. 4 weeks after the application the test is evaluated. In evaluating the test, the new growth is estimated and weighted in comparison with the control and the phytotoxicity is assessed. In this test, the plants treated with the active ingredients of Table 1 at application rates of up to 3000 g/ha show a marked reduction in new growth (less than 20% of the new growth in untreated control plants) without the test plants being at the same time damaged.

EXAMPLE B5

Growth regulation in soybeans

Soybeans of the variety "Hark" are sown in plastics containers containing a mixture of soil, peat and sand in a ratio of 6:3:1 and placed in a climatic chamber. By optimum temperature selection, illumination, application of fertilizer and watering, the plants develop after about 5 weeks to the 5 to 6 trifolia leaf stage. At that time, the plants are sprayed until thoroughly wet with an aqueous liquor of an active ingredient of the formula I. The active ingredient concentration is up to 100 g active ingredient/ha. The evaluation is carried out about 5 weeks after application of the active ingredient. In comparison with untreated control plants, the active ingredients according to the invention of Table 1 cause an increase in the number and weight of the pods in the main shoot.

EXAMPLE B6

Growth inhibition in cereals

*Hordeum vulgare* (summer barley) and *Secale* (summer rye) are sown by cereal type in a greenhouse in plastics pots containing sterilized soil and watered as required. After 21 days after sowing, the young shoots are sprayed with an aqueous spray liquor of an active ingredient from Table 1. The quantity of active ingredient is up to 100 g per hectare. 21 days after the application the growth of the cereal is assessed. In comparison with untreated controls, the treated plants show a reduction in new growth, and in some cases an increase in the diameter of the stalk.

EXAMPLE B7

Growth inhibition in grasses

The grasses *Lolium perenne, Poa pratensis, Festuca ovina, Dacylis glomerata* and *Cynodon dactylon* are sown in a greenhouse in plastics trays containing a soil/peat/sand mixture (6:3:1) and watered as required. The emerged grasses are cut back weekly to a height of 4 cm and, about 50 days after sowing and one day after the last cut, sprayed with an aqueous spray liquor of an active ingredient from Tables 1 and 2. The quantity of active ingredient is equivalent to up to 500 g of active ingredient per hectate. 21 days after application, the growth of the grasses is assesses.

The tested compounds of Table 1 cause a reduction in the new growth compared with the untreated control.

FORMULATION EXAMPLES

EXAMPLE F1

Formulation Examples for active ingredients of formula I' (%=percent by weight)

| (a) Emulsifiable concentrates | (a) | (b) | (c) |
| --- | --- | --- | --- |
| active ingredient according to Preparation Example 1 | 20% | 40% | 50% |
| calcium dodecylbenzenesulphonate | 5% | 8% | 5.8% |
| castor oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) |
|---|---|---|---|
| active ingredient according to Preparation Example 1 | 80% | 10% | 5% |
| ethylene glycol monomethyl ether | 20% | — | — |
| polyethylene glycol MW 400 | — | 70% | — |
| N—methyl-2-pyrrolidone | — | 20% | 5% |
| epoxidised coconut oil | — | — | 90% |

The solutions are suitable for use in the form of extremely fine droplets.

| (c) Granulates | (a) | (b) |
|---|---|---|
| active ingredient according to Preparation Example 1 | 5% | 10% |
| kaolin | 94% | — |
| highly dispersed silicic acid | 1% | — |
| attapulgite | — | 90% |

A solution of the active ingredient is sprayed onto the carrier and the solvent is then evaporated off in vacuo.

| (d) Dusts | (a) | (b) |
|---|---|---|
| active ingredient according to Preparation Example 1 | 2% | 5% |
| highly dispersed silicic acid | 1% | 5% |
| talcum | 97% | — |
| kaolin | — | 90% |

Dusts that are ready for use are obtained by intimately mixing the carriers with the active ingredient.

| (e) Wettable powders | (a) | (b) |
|---|---|---|
| active ingredient according to Preparation Example 1 | 20% | 60% |
| sodium lignosulphonate | 5% | 5% |
| sodium lauryl sulphate | — | 6% |
| octylphenolpolyethylene glycol ether (7-8 mols of ethylene oxide) | — | 2% |
| highly dispersed silicic acid | 5% | 27% |
| kaolin | 70% | — |

The active ingredient is mixed well with the additives and thoroughly ground in a suitable mill. A wettable powder is obtained which can be diluted with water to form a suspension of any desired concentration.

| (f) Extruder granulate | |
|---|---|
| active ingredient according to Preparation Example 1 | 10% |
| sodium lignosulphonate | 2% |
| carboxymethylcellulose | 1% |
| kaolin | 87% |

The active ingredient is mixed with the additives, ground and moistened with water. This mixture is extruded and then dried in an air stream.

| (g) Coated granulate | |
|---|---|
| active ingredient according to Preparation Example 1 | 3% |
| polyethylene glycol (MW 200) | 3% |
| kaolin | 94% |

The finely ground active ingredient is uniformly applied in a mixer to the kaolin moistened with polyethylene glycol. A dust-free coated granulate is obtained in this manner

| (h) Suspension concentrate | |
|---|---|
| active ingredient according to Preparation Example 1 | 40% |
| ethylene glycol | 10% |
| nonylphenolpolyethylene glycol ether (15 mols of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | ad 100% |

The active ingredient is intimately mixed with the additives. In this manner, a suspension concentrate is obtained from which suspensions of any desired concentration can be prepared by dilution with water.

We claim:

1. Compounds of the formula

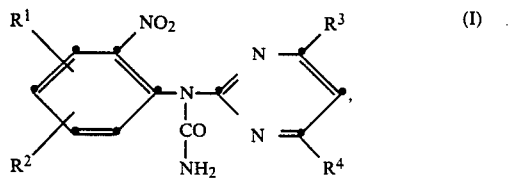

in which $R^1$ and $R^2$ each represents, independently of the other, hydrogen, halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkoxy-($C_1$–$C_4$)-alkyl, nitro or cyano, and $R^3$ and $R^4$ each represents, independently of the other, hydrogen, halogen, cyano, OH, SH, $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, mono-$C_1$–$C_4$-alkylamino, di-$C_1$–$C_4$-alkylamino, $C_1$–$C_4$-alkoxycarbonyl or $C_1$–$C_4$-alkoxy-($C_1$–$C_4$)-alkyl, and the salts and addition compounds thereof with acids, bases and complex formers.

2. Compounds of the formula I according to claim 1 in which $R^1$ represents hydrogen, halogen, $C_1$–$C_3$-alkyl, $C_1$–$C_3$-haloalkyl, $C_1$–$C_3$-alkoxy or $C_1$–$C_3$-alkoxycarbonyl, $R^2$ represents hydrogen, halogen, $C_1$–$C_3$-alkyl, nitro or cyano, and $R^3$ and $R^4$ each represents, independently of the other, hydrogen, halogen, $C_1$–$C_3$-alkyl, $C_1$–$C_3$-haloalkyl, $C_1$–$C_4$-alkoxy, $C_1$–$C_3$-haloalkoxy, $C_1$–$C_4$-alkylthio, amino, mono-$C_1$–$C_3$-alkylamino, di-$C_1$–$C_3$-alkylamino, cyano, $C_1$–$C_4$-alkoxycarbonyl or $C_1$–$C_3$-alkoxy-($C_1$–$C_3$)-alkyl.

3. Compounds of the formula I according to claim 1 in which
R$^1$ represents hydrogen, chlorine, methyl, trifluoromethyl, methoxy or ethoxycarbonyl,
R$^2$ represents hydrogen, chlorine, methyl or nitro,
R$^3$ represents hydrogen, fluorine, chlorine, methyl, ethyl, propyl, trifluoromethyl, methoxy, ethoxy, difluoromethoxy, 1,1,2,2-tetrafluoroethoxy, dimethylamino, ethoxycarbonyl or C$_1$–C$_4$-alkylthio, and
R$^4$ represents hydrogen, fluorine, chlorine, bromine, methyl, methoxymethyl, methoxyethyl, C$_1$–C$_4$-alkoxy, 1,1,2,2-tetrafluoroethoxy, dimethylamino, difluoromethoxy, fluoromethoxy, trifluoromethyl or C$_1$–C$_4$-alkylthio.

4. Compounds of the formula I according to claim 1 in which
R$^1$ represents hydrogen, methyl, methoxy, trifluoromethyl or Cl,
R$^2$ represents hydrogen or methyl,
R$^3$ represents methyl, ethyl, propyl, chlorine, trifluoromethyl, 1,1,2,2-tetrafluoroethoxy, methylthio, propylthio, ethoxy or methoxy, and
R$^4$ represents fluorine, chlorine, methyl, methoxy, methoxymethyl, difluoromethoxy, fluoromethoxy, trifluoromethyl or bromine.

5. Compounds of the I according to claim 1 in which R$^1$ is bonded in the 5-position of the phenyl system.

6. Compounds of the formula I according to claim 1 in which R$^2$ is bonded in the 6-position of the phenyl system.

7. Compounds of the formula I according to claim 1 in which R$^1$ and R$^2$ represent hydrogen, R$^3$ represents methoxy or methyl and R$^4$ represents chlorine, methyl, methoxy, trifluoromethyl, methoxymethyl or difluoromethoxy.

8. Compounds of the formula

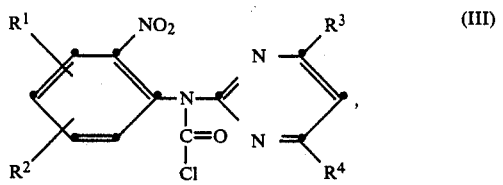

(III)

in which
R$^1$ and R$^2$ each represents, independently of the other, hydrogen, halogen, C$_1$–C$_6$-alkyl, C$_1$–C$_4$-haloalkyl, C$_1$–C$_4$-alkoxy, C$_1$–C$_4$-haloalkoxy, C$_1$–C$_4$-alkoxycarbonyl, C$_1$–C$_4$-alkoxy-(C$_1$–C$_4$)-alkyl, nitro or cyano, and
R$^3$ and R$^4$ each represents, independently of the other, hydrogen, halogen, cyano, C$_1$–C$_6$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, amino, mono-C$_1$–C$_4$-alkylamino, di-C$_1$–C$_4$-alkylamino, C$_1$–C$_4$-alkoxycarbonyl or C$_1$–C$_4$-alkoxy-(C$_1$–C$_4$)-alkyl.

9. Ureas of the formula

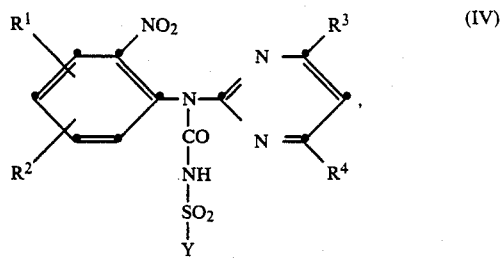

(IV)

in which
R$^1$ and R$^2$ each represents, independently of the other, hydrogen, halogen, C$_1$–C$_6$-alkyl, C$_1$–C$_4$-haloalkyl, C$_1$–C$_4$-alkoxy, C$_1$–C$_4$-haloalkoxy, C$_1$–C$_4$-alkoxycarbonyl, C$_1$–C$_4$-alkoxy-(C$_1$–C$_4$)-alkyl, nitro or cyano, and
R$^3$ and R$^4$ each represents, independently of the other, hydrogen, halogen, cyano, C$_1$–C$_6$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, amino, mono-C$_1$–C$_4$-alkylamino, di-C$_1$–C$_4$-alkylamino, C$_1$–C$_4$-alkoxycarbonyl or C$_1$–C$_4$-alkoxy-(C$_1$–C$_4$)-alkyl, and
Y represents halogen, C$_1$–C$_4$-alkoxy or phenoxy.

10. A herbicidal composition containing as active ingredient an effective amount compound of formula I according to claim 1 together with other adjuvants and/or carriers.

11. A plant growth-regulating composition containing as active ingredient an effective amount a compound of the formula I according to claim 1 together with other adjuvants and/or carriers.

12. A method of controlling undesired plant growth, characterised in that a herbicidally effective amount of an active ingredient of the formula I according to claim 1 is applied to the environment of the plant to be controlled.

13. A method according to claim 12 for the pre-emergence control of weeds in cereals, soya, cotton, maize, rice or rape.

14. A method of influencing plant growth, characterized in that an amount of an active ingredient of the formula I according to claim 1 that is effective for plant growth regulation is applied to the environment of the plant.

* * * * *